United States Patent
Tsuda

(10) Patent No.: US 10,531,840 B2
(45) Date of Patent: Jan. 14, 2020

(54) IMAGE DISPLAY DEVICE, IMAGE DISPLAY SYSTEM, IMAGE DISPLAY METHOD, AND PROGRAM

(71) Applicant: PANASONIC INTELLECTUAL PROPERTY MANAGEMENT CO., LTD., Osaka (JP)

(72) Inventor: Kenjiro Tsuda, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 114 days.

(21) Appl. No.: 15/558,430

(22) PCT Filed: Feb. 10, 2016

(86) PCT No.: PCT/JP2016/000686
§ 371 (c)(1),
(2) Date: Sep. 14, 2017

(87) PCT Pub. No.: WO2016/147545
PCT Pub. Date: Sep. 22, 2016

(65) Prior Publication Data
US 2018/0055458 A1    Mar. 1, 2018

(30) Foreign Application Priority Data

Mar. 19, 2015  (JP) ................................. 2015-056363

(51) Int. Cl.
*A61B 5/00* (2006.01)
*G06K 9/62* (2006.01)
(Continued)

(52) U.S. Cl.
CPC .......... *A61B 5/7425* (2013.01); *A61B 5/0033* (2013.01); *A61B 5/0037* (2013.01);
(Continued)

(58) Field of Classification Search
CPC .............................. A61B 5/0091; G06F 16/50
(Continued)

(56) References Cited

U.S. PATENT DOCUMENTS 8,090,166 B2 *  1/2012  Rappaport ............. A61B 5/107
                                                    382/128
2001/0053240 A1 * 12/2001  Oosawa ............... G06K 9/6203
                                                    382/128
(Continued)

FOREIGN PATENT DOCUMENTS

JP     2008-006188      1/2008
JP     2008-043524      2/2008
(Continued)

OTHER PUBLICATIONS

Search Report issued in International Patent Application No. PCT/JP2016/000686, dated May 17, 2016.

*Primary Examiner* — Tsung Yin Tsai
*Assistant Examiner* — Stephen M Brinich
(74) *Attorney, Agent, or Firm* — Greenblum & Bernstein, P.L.C.

(57) ABSTRACT

Image display device includes image outputting unit, part moving unit, and matching degree score calculating unit. Image outputting unit outputs, among a plurality of images obtained by performing a multilayered anatomy in a plurality of parts of a human body, an image of one layer of one part as a current image. Part moving unit acquires a part moving instruction after current image is output. Matching degree score calculating unit calculates a matching degree score indicating the matching degree between the organ included in current image and a candidate image by comparing label information indicating the organ included in current image and label information indicating the organ included in candidate image, with respect to each of a plurality of candidate images of a movement target part.

(Continued)

Image outputting unit outputs candidate image in which a maximum matching degree score is calculated as a new current image.

14 Claims, 12 Drawing Sheets

(51) Int. Cl.
    *G06K 9/00*         (2006.01)
    *G06F 3/147*       (2006.01)
    *G06F 3/14*        (2006.01)
    *G06F 16/00*       (2019.01)
    *G09G 5/14*        (2006.01)
    *G06T 7/00*        (2017.01)

(52) U.S. Cl.
    CPC .............. *A61B 5/0077* (2013.01); *G06F 3/14* (2013.01); *G06F 3/147* (2013.01); *G06F 16/00* (2019.01); *G06K 9/00718* (2013.01); *G06K 9/6202* (2013.01); *G06K 9/6203* (2013.01); *G06K 9/6253* (2013.01); *G06T 7/0012* (2013.01); *G09G 5/14* (2013.01); *A61B 5/7246* (2013.01); *A61B 2560/0475* (2013.01); *A61B 2576/00* (2013.01); *G06K 2209/051* (2013.01); *G09G 2380/08* (2013.01)

(58) Field of Classification Search
    USPC .................. 382/128, 130–132, 155, 165, 181
    See application file for complete search history.

(56) References Cited

U.S. PATENT DOCUMENTS

| | | |
|---|---|---|
| 2009/0279753 A1 | 11/2009 | Sakaida |
| 2010/0231605 A1 | 9/2010 | Moriya et al. |
| 2011/0058726 A1* | 3/2011 | Markwardt ........... G06T 7/0014 |
| | | 382/132 |
| 2012/0299818 A1 | 11/2012 | Li et al. |
| 2014/0285525 A1 | 9/2014 | Okusu et al. |

FOREIGN PATENT DOCUMENTS

| | | |
|---|---|---|
| JP | 2012-247880 | 12/2012 |
| JP | 2014-184048 | 10/2014 |

* cited by examiner

| PART NAME | LAYER NUMBER | IMAGE |
|---|---|---|
| RIGHT CHEST PART | 1 | IMAGE 1 |
| RIGHT CHEST PART | 2 | IMAGE 2 |
| RIGHT CHEST PART | 3 | IMAGE 3 |
| RIGHT CHEST PART | 4 | IMAGE 4 |
| RIGHT UPPER LIMB | 1 | IMAGE 5 |
| RIGHT UPPER LIMB | 2 | IMAGE 6 |
| RIGHT UPPER LIMB | 3 | IMAGE 7 |

| PART NAME | LAYER NUMBER | LABEL NAME | LABEL POSITION |
|---|---|---|---|
| RIGHT CHEST PART | 2 | BLOOD VESSEL 1 | P1 |
| RIGHT CHEST PART | 3 | BLOOD VESSEL 1 | P2 |
| RIGHT CHEST PART | 3 | NERVE 1 | P3 |
| RIGHT CHEST PART | 4 | BLOOD VESSEL 1 | P4 |
| RIGHT CHEST PART | 4 | NERVE 1 | P5 |
| RIGHT CHEST PART | 4 | NERVE 2 | P6 |
| RIGHT CHEST PART | 4 | MUSCLE 2 | P7 |
| RIGHT UPPER LIMB | 2 | BLOOD VESSEL 1 | P8 |
| RIGHT UPPER LIMB | 3 | BLOOD VESSEL 1 | P9 |
| RIGHT UPPER LIMB | 3 | NERVE 1 | P10 |
| RIGHT UPPER LIMB | 3 | MUSCLE 1 | P11 |

*FIG. 4*

| REFERENCE PART NAME | DIRECTION | ADJACENT PART NAME |
|---|---|---|
| RIGHT CHEST PART | RIGHT | RIGHT UPPER LIMB |
| RIGHT UPPER LIMB | LEFT | RIGHT CHEST PART |

| PART NAME | LAYER NUMBER | LABEL NAME | POSITION IN IMAGE | IMPORTANCE DEGREE |
|---|---|---|---|---|
| RIGHT CHEST PART | 2 | BLOOD VESSEL 1 | P1 | HIGH |
| RIGHT CHEST PART | 3 | BLOOD VESSEL 1 | P2 | HIGH |
| RIGHT CHEST PART | 3 | NERVE 1 | P3 | HIGH |
| RIGHT CHEST PART | 4 | BLOOD VESSEL 1 | P4 | HIGH |
| RIGHT CHEST PART | 4 | NERVE 1 | P5 | HIGH |
| RIGHT CHEST PART | 4 | NERVE 2 | P6 | MEDIUM |
| RIGHT CHEST PART | 4 | MUSCLE 2 | P7 | MEDIUM |
| RIGHT UPPER LIMB | 2 | BLOOD VESSEL 1 | P8 | HIGH |
| RIGHT UPPER LIMB | 3 | BLOOD VESSEL 1 | P9 | HIGH |
| RIGHT UPPER LIMB | 3 | NERVE 1 | P10 | HIGH |
| RIGHT UPPER LIMB | 3 | MUSCLE 1 | P11 | LOW |

FIG. 14

| PART NAME | PART POSITION |
|---|---|
| RIGHT CHEST PART | Q1 |
| RIGHT UPPER LIMB | Q2 |

IMAGE DISPLAY DEVICE, IMAGE DISPLAY SYSTEM, IMAGE DISPLAY METHOD, AND PROGRAM

TECHNICAL FIELD

The present invention relates to an image display device, an image display system, an image display method, and a program, and particularly, to a technique for displaying an anatomical image of a human body.

BACKGROUND ART

Recently, as a lot of medical information has been accumulated in a field of medical treatment or medical science, a demand for a user interface for easily browsing desired medical information from enormous medical information has been intensifying.

For example, PTL 1 discloses a medical information display device that proposes examination information of an instructed diagnosed part of a patient to a user (for example, doctor) when the user instructs the diagnosed part of the patient on an external image of a human body.

PTL 1 points out a problem that there may be a case in which a user cannot instruct one desired organ on the external image in a distinguished manner, if a plurality of organs (for example, lung and heart) are present to overlap with each other in one part (for example, chest) of the human body.

With respect to this problem, the medical information display device of PTL 1 enables a user to instruct a desired organ in one image among a plurality of anatomical images using the plurality of anatomical images schematically illustrating organs and tissues which sequentially appear at the time of anatomizing a human body.

CITATION LIST

Patent Literature

PTL 1: Japanese Patent Unexamined Publication No. 2012-247880

SUMMARY OF THE INVENTION

The present inventors are developing a medical image display system. The image display system accumulates a plurality of images obtained by respectively executing a local and a multilayered anatomy on a plurality of parts of a human body, and proposes the images when the user (for example, a doctor or a medical student) browses.

In the image display system, there is a case in which the user who browsing an image wants to move a point of interest in a depth direction of a human body. In this case, by switching a display to an image of another layer of the multilayered anatomy being currently referenced, the user can smoothly move the point of interest in the depth direction of the human body. The idea of sequentially proposing the plurality of images respectively having different depths from a body surface is also in common with the idea of PTL 1.

However, there is also a case in which the user may want to move the point of interest to another part of the human body. In a case in which a number of images are recorded by the multilayered anatomy in a movement target part, it is not always clear which image is an appropriate image that needs to be proposed to a user. If the user needs to sequentially reference the plurality of images in the movement target part in order to reach the desired image, convenience of the image display system is greatly impaired.

Here, the disclosure is to provide an image display device which is capable of displaying an appropriate image in accordance with the part moving instruction from the user, among the plurality of images obtained by photographing the organ on which the multilayered anatomy is performed in a plurality of parts of the human body.

An image display device according to an aspect of the disclosure is provided with an image outputter, a part mover, and a matching degree score calculator. The image outputter outputs, among a plurality of images obtained by performing a multilayered anatomy and photographing the organ in a plurality of parts of a human body, an image of one layer in the multilayered anatomy of one part as a current image. The part mover acquires a part moving instruction which instruct to display a different part from the part of the current image after the current image is output. The matching degree score calculator calculates a matching degree score indicating a matching degree between at least one organ included in a candidate image and at least one organ included in the current image by comparing label information indicating the organ included in the current image with label information indicating the organ included in the candidate image, with respect to each of a plurality of the candidate images which are the plurality of images of individual layers corresponding to a part instructed to be displayed by the part moving instruction in the plurality of images. The image outputter outputs the candidate image in which a maximum matching degree score is calculated as a new current image.

These general or specific aspects may be realized by systems, methods, integrated circuits, computer programs, or recording mediums such as computer readable CD-ROMs, or may be realized by an arbitrary combination of the systems, methods, integrated circuits, computer programs, or recording mediums.

BRIEF DESCRIPTION OF DRAWINGS

FIG. 2 is a diagram illustrating an example of image information according to the first exemplary embodiment.

FIG. 3 is a diagram illustrating an example of label information according to the first exemplary embodiment.

FIG. 4 is a diagram illustrating an example of part arrangement information according to the first exemplary embodiment.

FIG. 13 is a diagram illustrating an example of label information according to a second exemplary embodiment.

FIG. 14 is a diagram illustrating an example of part arrangement information according to a modification example.

DESCRIPTION OF EMBODIMENTS

Hereinafter, an image display system according to an aspect of the invention will be described in detail with reference to drawings.

All exemplary embodiments to be described later indicate specific examples of the invention. Numerical values, shapes, materials, configuration components, arrangement positions and connection shapes of the configuration components, steps, orders of the steps, and the like illustrated in exemplary embodiments as follows are examples, and are not intended to limit the invention. In addition, among the configuration components in the exemplary embodiments as follows, configuration components which are not disclosed in the independent claim indicating the highest concept will be described as arbitrary configuration components.

(First Exemplary Embodiment)

An image display system according to a first exemplary embodiment is an image display system which displays an appropriate image in accordance with a part moving instruction of a user, in a plurality of images obtained by performing a multilayered anatomy and photographing organs in a plurality of parts of a human body.

Figure 1:
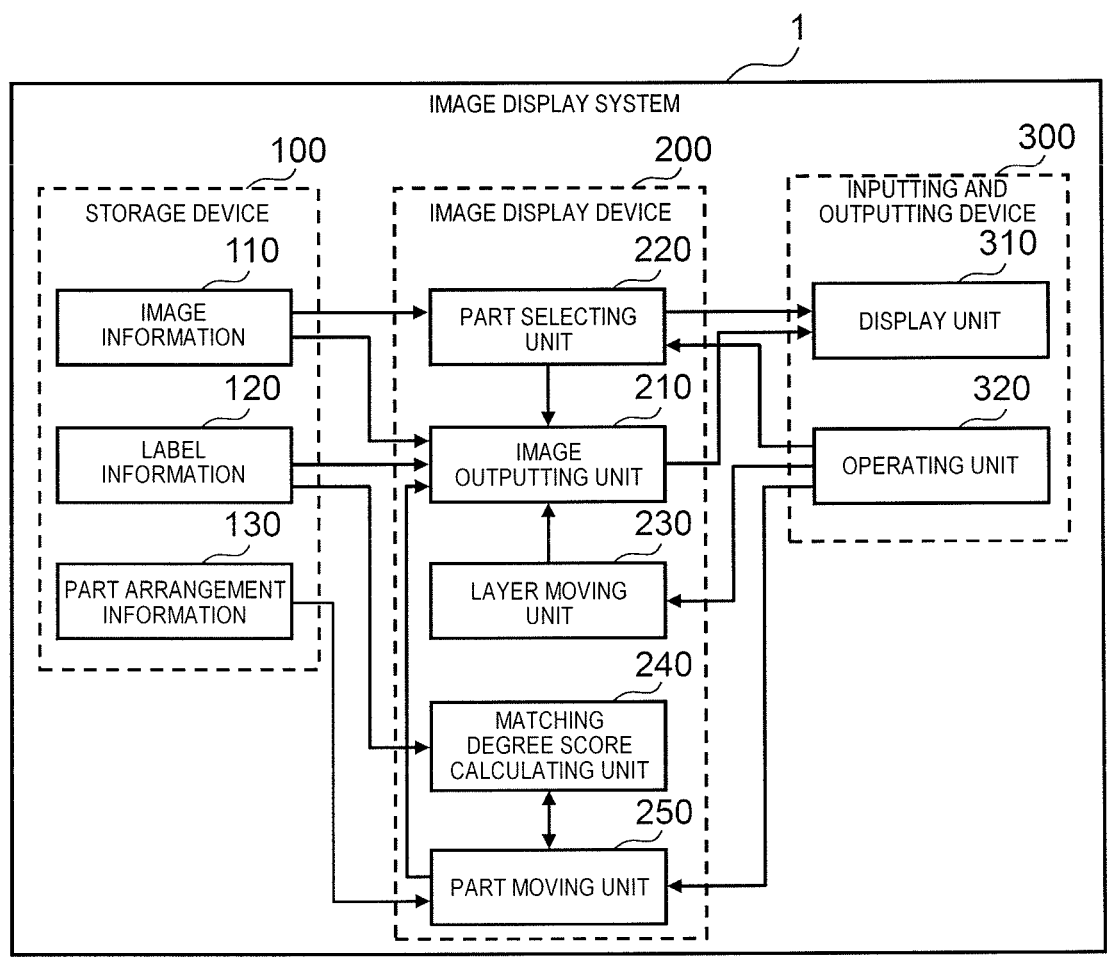
FIG. 1 is a block diagram illustrating an example of a functional configuration of an image display system according to a first exemplary embodiment.

FIG. 1 is a block diagram illustrating an example of a functional configuration of the image display system according to the first exemplary embodiment.

As illustrated in FIG. 1, an image display system 1 is provided with storage device 100, image display device 200, and inputting and outputting device 300.

Storage device 100 is a device which stores various data items including images relating to the multilayered anatomy being performed on each of the plurality of parts of a human body, and image information 110, label information 120, and part arrangement information 130 are included in the data.

Image information 110 is information indicating the image photographed by the multilayered anatomy in correlation with a part and a layer in which the image is photographed.

Label information 120 is information indicating a label indicating one or more organ included in the image in correlation with the image.

Part arrangement information 130 is information indicating an arrangement of parts on which the multilayered anatomy is performed.

These pieces of the information will be described in detail later with specific examples.

Storage device 100 may be constituted by, for example, a hard disk device or a semiconductor memory device.

Image display device 200 is a device which outputs data stored in storage device 100 in accordance with the instruction of the user, and is provided with image outputting unit 210, part selecting unit 220, layer moving unit 230, matching degree score calculating unit 240, and part moving unit 250.

Image outputting unit 210 outputs an image of one layer in the multilayered anatomy of one part as a current image. Here, the current image means an image of a part and a layer on which the user is currently focused, and, in image display system 1, an image which is output from image outputting unit 210 and recently displayed by display unit 310 is defined as the current image.

Part selecting unit 220 proposes a list of the parts on which the multilayered anatomy is performed to the user. When receiving a part selecting instruction for selecting one part in the list, image outputting unit 210 outputs an image of a body surface layer in the multilayered anatomy in the selected part as a current image.

When layer moving unit 230 receives a layer moving instruction in which a different layer in the same part as the current image is defined as a movement target layer after the current image is output, image outputting unit 210 outputs the image of the movement target layer as a new current image.

Matching degree score calculating unit 240 calculates a matching degree score indicating a matching degree of organs included in two images by comparing pieces of label information relating to two images with each other.

When part moving unit 250 receives a part moving instruction in which a different part from that of the current image is indicated as a movement target part after the current image is output, matching degree score calculating unit 240 calculates a matching degree score with respect to a candidate image which is an image of each layer of the movement target part. Image outputting unit 210 outputs the candidate image of which a maximum matching degree score is calculated as a new current image.

Image display device 200 may be constituted by a computer including, for example, a microprocessor or a memory which is not illustrated. A part or all of functions of configuration components of image display device 200 may be achieved when a microprocessor executes a program which is stored in a memory in advance. In addition, a part or all of the functions of the configuration components of image display device 200 may be also achieved by an exclusive hardware circuit.

Inputting and outputting device 300 is a device for having a conversation with a user, and includes display unit 310 and operating unit 320.

Display unit 310 proposes various data items including images received from image display device 200 to a user.

Operating unit 320 receives operations indicating various instructions from the user, and transmits instructions indicated by the received operations to image display device 200.

Inputting and outputting device 300 may be configured with, for example, a touch panel, and may be also configured with a combination of a display, a keyboard, and a mouse.

Next, an operation of image display system 1 which is configured as described above will be described.

First, a specific example of the data stored in storage device 100 is described, and then, the operation of image display system 1 will be described on the basis of the specific example of the data.

FIG. 2 is a diagram illustrating an example of the image information.

Image information 110 illustrated in FIG. 2 indicates an image obtained by the multilayered anatomy in correlation with a part name and a layer number on which the multilayered anatomy is executed. The layer number indicates a stage of progress of the multilayered anatomy, and for example, it is indicated a deep layer from the body surface as the number increases. In this case, a first layer indicates the body surface layer.

For the sake of simple description, one multilayered anatomy corresponds to one part name. In a case in which a plurality of the multilayered anatomies are executed on the same part, the individual multilayered anatomy is distinguished, for example, by attaching a serial number to each part. In addition, one image corresponds to one layer number. In a case in which a plurality of images on the same layer are photographed, the individual image is distinguished, for example, by attaching a branch number to the layer number. Accordingly, one image is distinguished by a set of the part name and the layer number.

As an example, FIG. 2 illustrates image 1 to image 4 of four layers that the multilayered anatomy is executed on a right chest part, and image 5 to image 7 of three layers that the multilayered anatomy is executed on a right upper limb. Each image may be a normal planar image, or may be a parallax stereoscopic image.

FIG. 3 is a diagram illustrating an example of the label information.

Label information 120 illustrated in FIG. 3 indicates a label name indicating one or more organs included in an image and a label position which is a position inside the image including the organ in correlation with the part name and the layer number of the multilayered anatomy. A set of the part name and the layer number is used for distinguishing one image, and thus it is possible to say that the label name and the position inside the image correspond to the image. The label position is illustrated as a two-dimensional coordinate if the image is a general planar image, and is illustrated as a three-dimensional coordinate if the image is a parallax stereoscopic image.

As an example, FIG. 3 illustrates that blood vessel 1 is included in position P1 of an image of a second layer of the right chest part, blood vessel 1 and nerve 1 are respectively included in positions P2 and P3 of an image of a third layer of the right chest part, and blood vessel 1, nerve 1, nerve 2, and muscle 2 are respectively included in positions P4, P5, P6, and P7 of an image of a fourth layer of the right chest part. In addition, it is illustrated that blood vessel 1 is included in position P8 of the image of the second layer of the right upper limb, and blood vessel 1, nerve 1, and muscle 1 are respectively included in positions P9, P10, and P11 of the image of the third layer of the right upper limb.

FIG. 4 is a diagram illustrating an example of the part arrangement information.

Part arrangement information 130 illustrated in FIG. 4 indicates a part adjacent to a reference part and an adjacent direction in correlation with a part name which becomes a reference.

As an example, FIG. 4 illustrates that the right upper limb is adjacent to a right side of the right chest part, and the right chest part is adjacent to a left side of the right upper limb. Moreover, the adjacent direction indicated by part arrangement information 130 is a direction of a human body, and a right side and a left side in the direction are reversed with respect to a direction in the displayed image.

Figure 5:
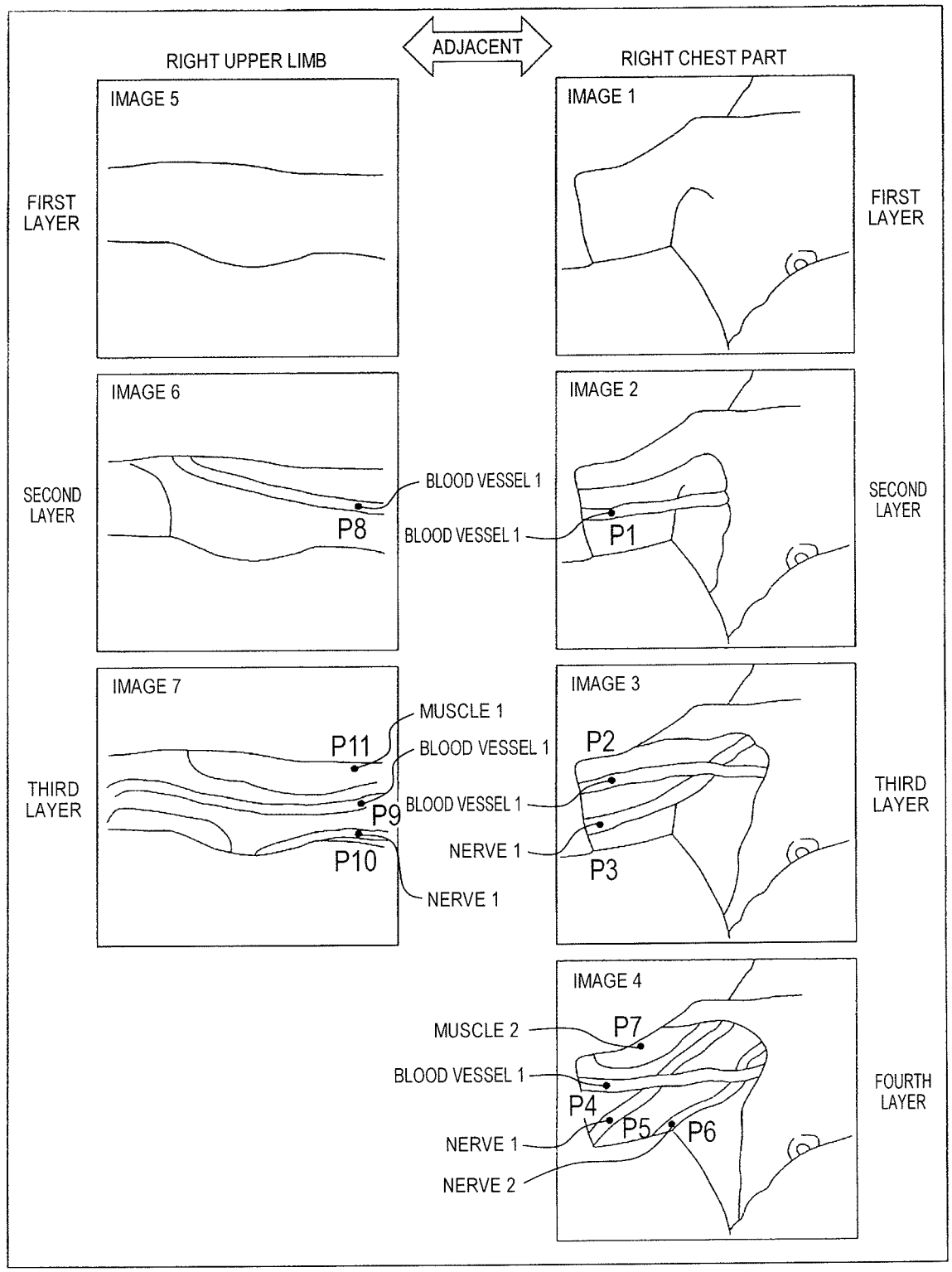
FIG. 5 is an explanatory diagram schematically illustrating a specific example of the image information, the label information, and the part arrangement information according to the first exemplary embodiment.

FIG. 5 is an explanatory diagram schematically illustrating a specific example of image information 110, label information 120, and part arrangement information 130.

FIG. 5 illustrates an example of image 1 to image 4 of the first layer to the fourth layer of the right chest part, and image 5 to image 7 of the first layer to the third layer of the right upper limb in accordance with image information 110 of FIG. 2. In addition, the label position and the label name are illustrated in images 2 to 4, 6, and 7 in accordance with the label information of FIG. 3. The right chest part and the right upper limb are illustrated to be adjacent to each other in accordance with part arrangement information 130 of FIG. 4.

Such image information 110, label information 120, and part arrangement information 130, for example, are accumulated in storage device 100 through works such as image correction, labeling, and specification of adjacent parts by a doctor or a staff, based on the image photographed by the multilayered anatomy.

Then, when image display device 200 starts to operate, part selecting unit 220 acquires a list of different parts from those of image information 110. Also, a part list screen displaying the acquired list of the parts is produced, and the part list screen is displayed on display unit 310.

Figure 6:
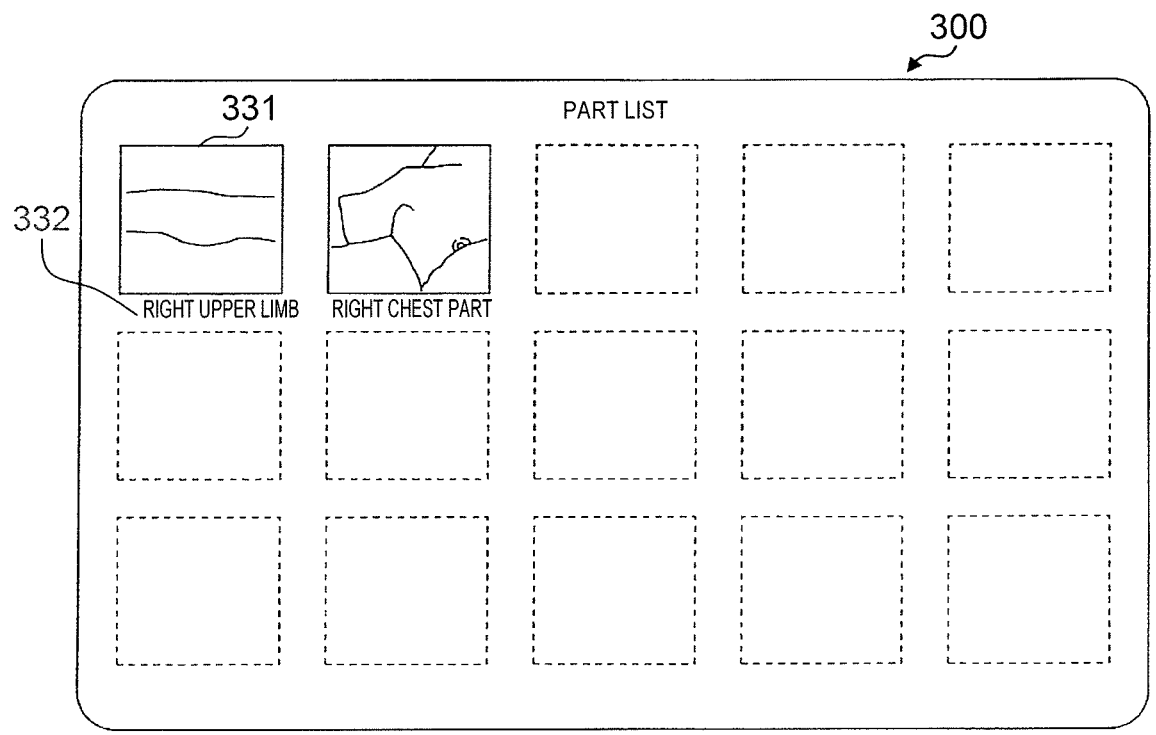
FIG. 6 is a diagram illustrating an example of a part list screen according to the first exemplary embodiment.

FIG. 6 is a diagram illustrating an example of the part list screen.

As illustrated in FIG. 6, a list of thumbnail image 331 and part name 332 of the image of the first layer (body surface layer) of each part included in image information 110 are displayed on the part list screen. On the part list screen, thumbnail image 331 may not need to be illustrated, and only part name 332 may be displayed. In addition, it is not illustrated, a simple description of the multilayered anatomy of each part may be recorded in storage device 100, and then the description may be displayed on the part list screen. A user can select a part to browse by tapping thumbnail image 331 or part name 332 on the part list screen.

When part selecting unit 220 receives a part selecting instruction by a user through operating unit 320, image outputting unit 210 is notified to output the image of the instructed part and the first layer (body surface layer) as a current image.

Image outputting unit 210 generates a current image displaying screen including the image of the notified part and layer as a current image, and the current image displaying screen is displayed on display unit 310.

Figure 7:
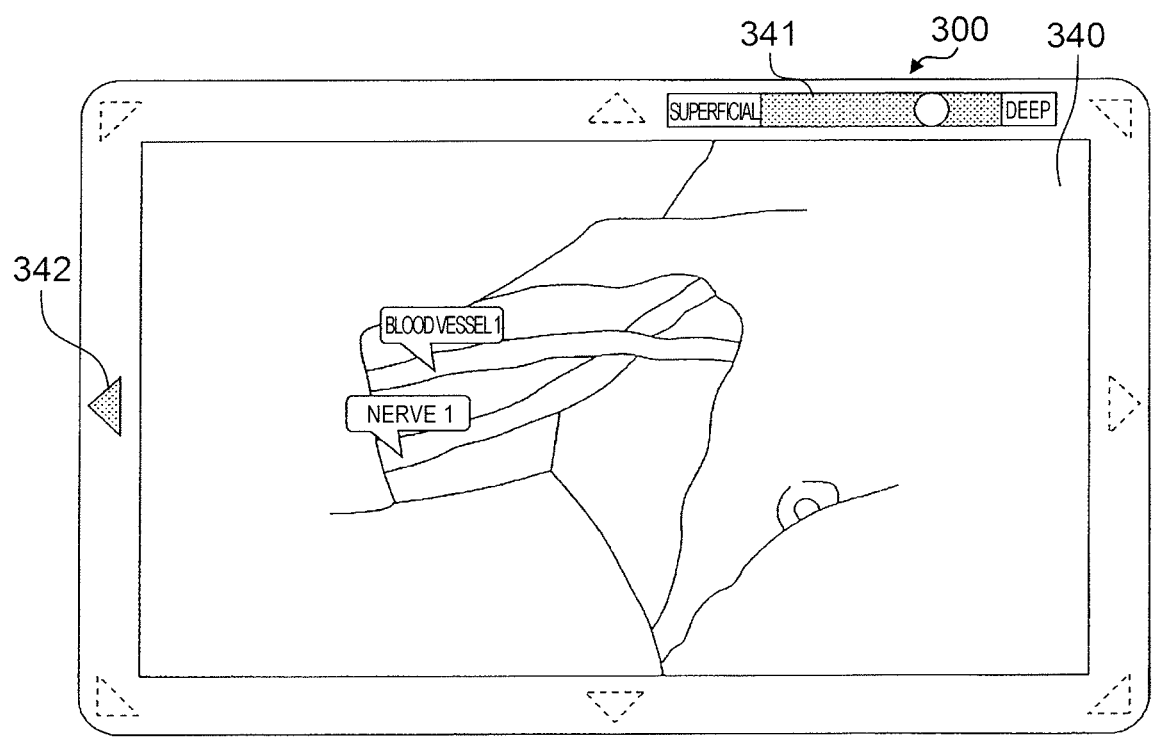
FIG. 7 is a diagram illustrating an example of a current image displaying screen according to the first exemplary embodiment.

FIG. 7 is diagram illustrating an example of the current image displaying screen.

FIG. 7 illustrates an example of the current image displaying screen in which the image of the third layer of the right chest part is included as the current image. On the current image displaying screen of FIG. 7, for example, after the right chest part on the part list screen of FIG. 6 is selected and the image of the first layer (the body surface layer) of the right chest part is displayed, the layers are moved so as to be able to reach the image of the third layer.

On the current image displaying screen, current image 340 is displayed on the center with a label, and layer moving bar 341 and part moving button 342 are displayed on a periphery of the screen. Part moving button 342 may be displayed only in a direction where an adjacent part is present in accordance with part arrangement information 130. The user can instruct movement to another layer from a current part by dragging layer moving bar 341, and can instruct movement to the adjacent part by tapping part moving button 342.

When layer moving unit 230 receives the layer moving instruction by a user through operating unit 320, image outputting unit 210 is notified to output the image of the instructed layer in the same part as the current image as a new current image. Image outputting unit 210 generates the current image displaying screen including the image in the notified part and layer as a new current image, and displays the screen on display unit 310.

As a result, since displaying by display unit 310 is switched to an image of the instructed layer from the current image by the user, the user can smoothly move a point of interest in a depth direction of a human body.

With respect to that, when the user instructs movement to the adjacent part, as described above, among the images of a plurality of the layers of the movement target part, it is necessary to switch the displaying to an image of an appropriate layer where a user can smoothly move a point of interest. Here, in image display system 1, such switching is realized by matching degree score calculating unit 240 and part moving unit 250.

Hereinafter, operations of matching degree score calculating unit 240 and part moving unit 250 will be described in detail.

Figure 8:
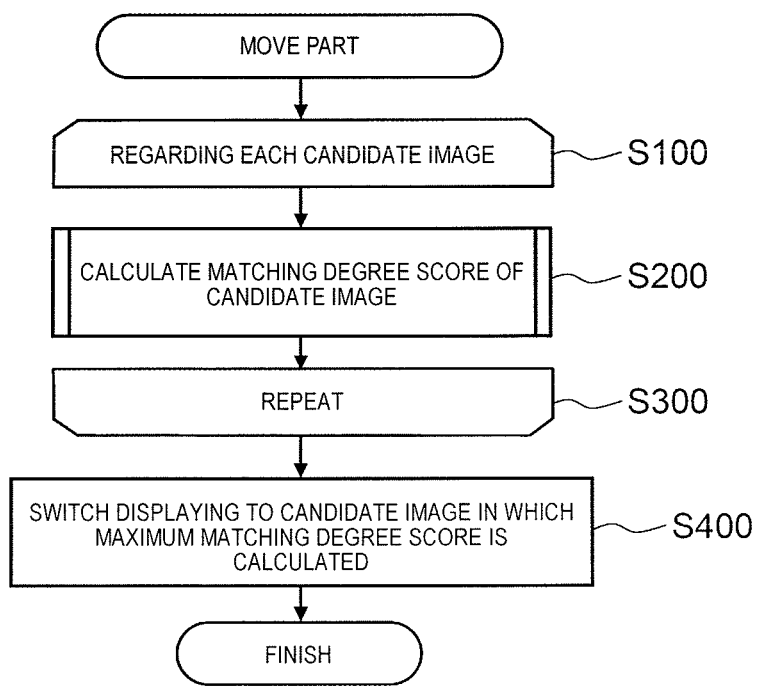
FIG. 8 is a flow chart illustrating an example of a part moving process according to the first exemplary embodiment.

FIG. 8 is a flow chart illustrating an example of the part moving process. The part moving process is executed when the user instructs movement to a part (including adjacent part) different from that of the current image.

Specifically, when part moving unit 250 receives the part moving instruction by the user through operating unit 320, with respect to a candidate image which is the image of each layer of the instructed movement target part, the matching degree score between the candidate image and the current image is calculated (S100 to S300). The matching degree score is a score indicating a matching degree of organs included in two images (here, candidate image and current image), and is calculated by matching degree score calculating unit 240 based on label information 120. Part moving unit 250 outputs a candidate image of which a maximum matching degree score is calculated as a new current image using image outputting unit 210 (S400).

Figures 9, 10:
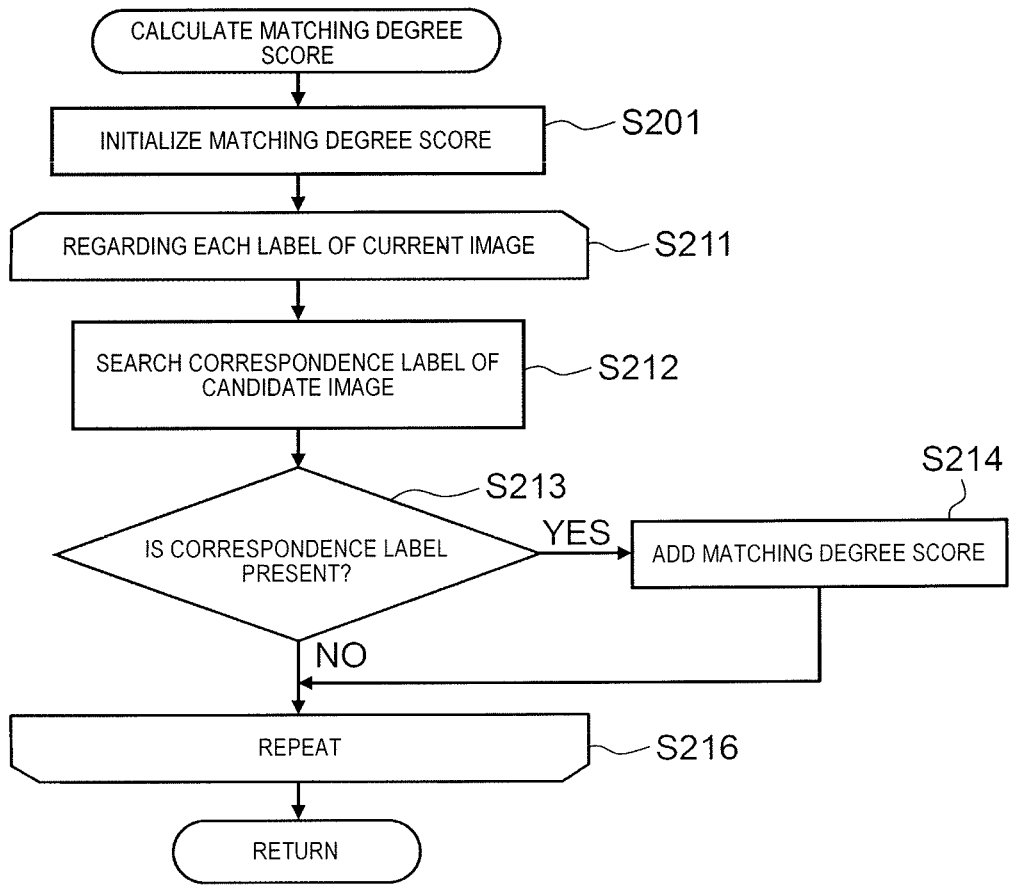
FIG. 9 is a flow chart illustrating an example of a matching degree score calculating process according to the first exemplary embodiment.
FIG. 10 is a diagram illustrating a calculated result of a matching degree score according to the first exemplary embodiment.

FIG. 9 is a flow chart illustrating a detailed example of the matching degree score calculating process being executed by Step S200 of FIG. 8. In the example of FIG. 9, the matching degree score, of the candidate image, is added for each common organ is commonly included in the current image and in the candidate image.

Specifically, when the current image and the candidate image of which the matching degree scores are necessary to be calculated are notified from part moving unit 250, matching degree score calculating unit 240 initializes the matching degree score to a predetermined value such as zero (S201). With reference to label information 120, it is determined whether or not a correspondence label indicating the common organ is also present in the candidate image for each label included in the current image, and if the correspondence label is present, a predetermined score is added to the matching degree score (for example, one point) (S211 to S216). If the amount of score to be added for each the common organ is set to one point, the number of the common organs is calculated as the matching degree score.

The correspondence label is determined by, for example, being matched with the label name. However, like the blood vessel and the nerve that change their name as they branch different parts of the connected same organ may be expressed with different label names. In this case, the correspondence label cannot be determined due to the matching with the label name, the correspondence label may be determined using, for example, a compatible information indicating the same organ, which is separated from the label name. The compatible information may be, for example, an alias table of the label name or an identification number for identifying the same organ.

FIG. 10 is a diagram illustrating an example of a calculated result of the matching degree score.

FIG. 10 illustrates the matching degree scores which are calculated with respect to images of each layer of the right upper limb, in a case of instructing movement to the right upper limb which is the adjacent part, from the images of the third layer of the right chest part which are current images, in accordance with the label information of FIG. 3 and a calculating method of FIG. 9.

As illustrated in FIG. 10, as the matching degree score, the number of the correspondence labels in the candidate image, that is, the number of the common organs being included in both the candidate image and the current image is calculated. Such a calculated result is, for example, temporally stored in a local memory being secured in the part moving process, and is referenced by part moving unit 250.

As described above, according to image display system 1, in accordance with the part moving instruction by a user, displaying by display unit 310 is switched from the current image to an image having a maximum matching degree of the organ with the current image among the plurality of images in the movement target part. As a result, the user is hard to lose the organ, for example, in a case of tracking and referring traveling of the blood vessel or the nerve, and can smoothly move a point of interest to the movement target part.

Moreover, the matching degree score calculating process is not limited to the example of FIG. 9. Hereinafter, several modification examples of the matching degree score calculating process will be described.

Figure 11:
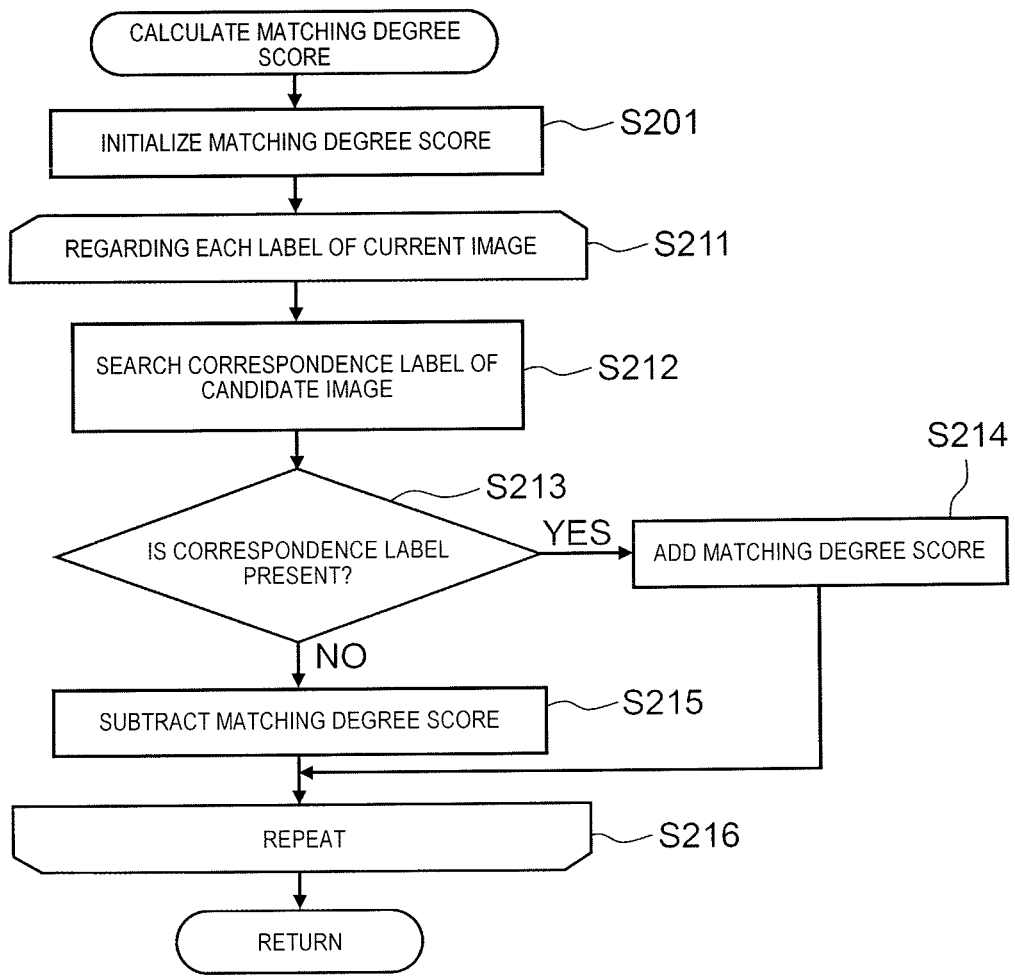
FIG. 11 is a flow chart illustrating another example of the matching degree score calculating process according to the first exemplary embodiment.

FIG. 11 is a flow chart illustrating another example of the matching degree score calculating process. Regarding the matching degree score calculating process of FIG. 11, a step of decrementing the matching degree score for a missing organ which is included in the current image but not included in the candidate image is added to the matching degree score calculating process of FIG. 9.

Specifically, in a case in which the correspondence label is not present in the candidate image (NO in S213), matching degree score calculating unit 240 decrements a predetermined score (for example, one point) from the matching degree score (S215). When the amount of score decremented for each missing organ is set to one point, the number of the missing organs is decremented from the matching degree score.

The candidate image in which fewer organs are missing can be displayed as a new current image, in accordance with the matching degree score calculated in such a manner.

Decrement of score due to the missing organ illustrated in FIG. 11 may be performed, for example, in order to narrow down the candidate images among a plurality of candidate images in a case in which the same maximum matching degree score with respect to the plurality of the candidate images is calculated by the matching degree score calculating process of FIG. 9.

Figure 12:
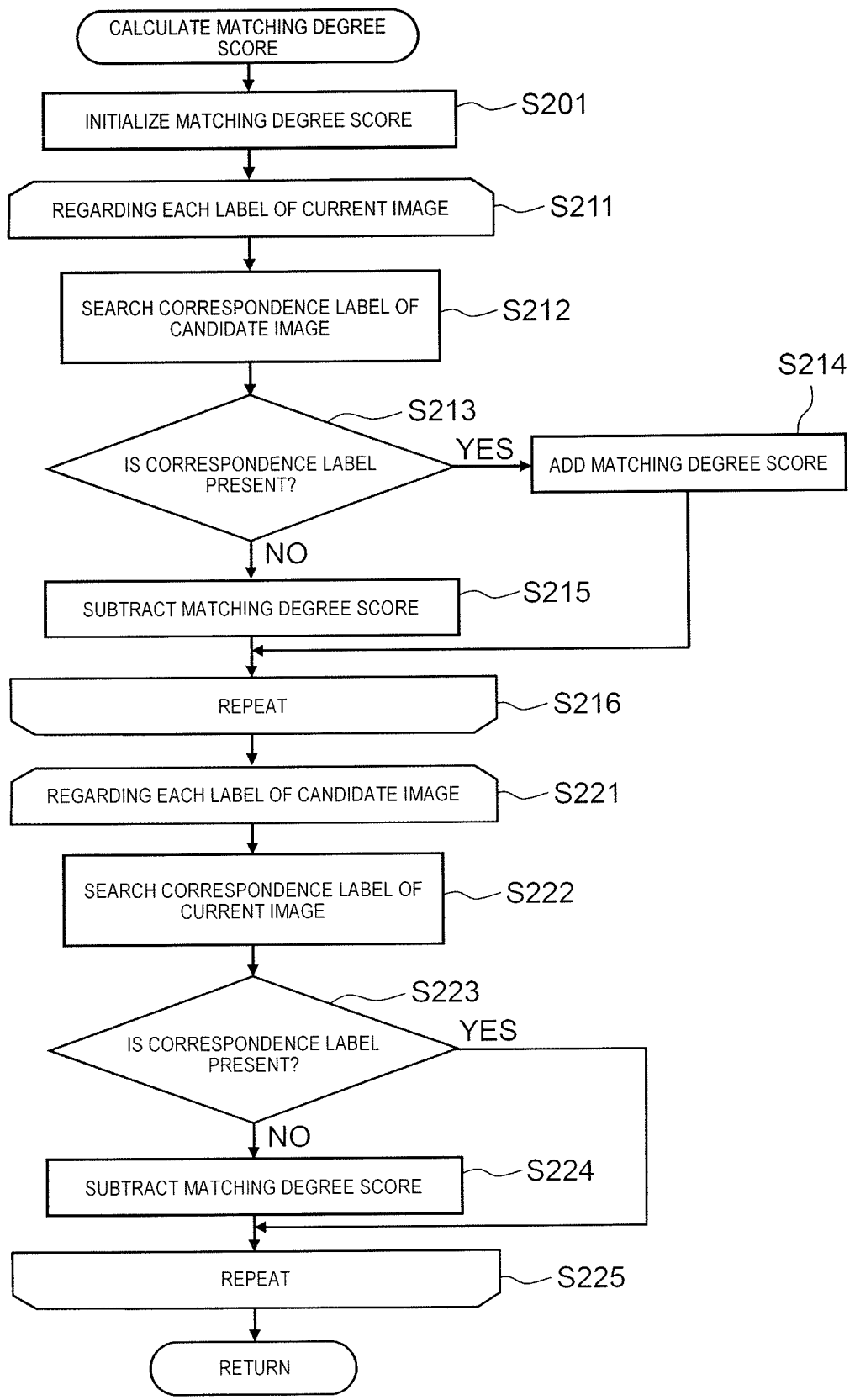
FIG. 12 is a flow chart illustrating still another example of the matching degree score calculating process according to the first exemplary embodiment.

FIG. 12 is a flow chart illustrating still another example of the matching degree score calculating process.

In the matching degree score calculating process of FIG. 12, a step of decrementing the matching degree score for an extra organ, which is included in the candidate image but is not included in the current image, is added after the matching degree score calculating process of FIG. 11.

Specifically, with reference to label information 120, matching degree score calculating unit 240 determines whether or not the correspondence label is present in the current image for each label included in the candidate image, and decrements a predetermined score (for example, one point) from the matching degree score if the correspondence label is not present (S221 to S225). If the amount of score decremented for each extra organ is set to one point, the number of the extra organs is subtracted from the matching degree score.

In accordance with the matching degree score calculated in such a manner, the candidate image in which fewer extra organs are missing can be displayed as a new current image.

The decrement of score due to the extra organ illustrated in FIG. 12 may be performed, for example, in order to narrow down the candidate images among the plurality of candidate images in a case in which the same maximum matching degree score with respect to the plurality of the candidate images is calculated by the matching degree score calculating process of FIG. 9 or FIG. 11.

According to the matching degree score calculating process of the modification examples, the candidate image in which fewer organs are missing or fewer extra organs are included can be displayed as a new current image. As a result, losing of attentiveness of a user due to the missing organ or the extra organ is reduced, and thereby making it possible to smoothly move a point of interest to the movement target part.

(Second Exemplary Embodiment)

In the first exemplary embodiment, the example is described in which the matching degree score, to which the number of each of the common organs, the missing organ, and the extra organ is reflected by setting both the amount of the score added and the amount of the score decremented of the matching degree score to one point, is calculated; however, the amount of the score added and the amount of the score decremented of the matching degree score are not limited to the example.

For example, at least one of the amount of the score added and the amount of the score decremented of the matching degree score may be set to the amount different in accordance with an importance degree of the organ for each organ. That is, the matching degree score may be weighted with the importance degree of the organ. The importance degree of each organ is represented by, for example, the label information.

FIG. 13 is a diagram illustrating an example of the label information according to the second exemplary embodiment.

Label information 120a illustrated in FIG. 13 is constituted by adding an importance degree to label information 120 of FIG. 3. The importance degree is represented by correlating to importance degree with an image and a label name when browsing the organs. Although a specific notation or meaning of the importance degree is not particularly limited, as an example, the importance degree is set to three stages of a high, a medium, and a low, an organ being referenced by a plurality of diagnosis and treatment departments may be represented by the high, an organ being referenced by only a diagnosis and treatment department in charge where a multilayered anatomy is executed may be represented by the medium, and an organ being focused by only the multilayered anatomy may be represented by the low.

Such label information 120a is accumulated in storage device 100, for example, through a certain work of an importance degree by a doctor or a staff based on an image photographed by the multilayered anatomy.

The matching degree score calculating process illustrated in FIG. 9, FIG. 11, and FIG. 12 is changed as follows corresponding to label information 120a having an importance degree.

In Step S214, a score which differs in an importance degree of the organ of the current image is added to the matching degree score. The amount of the score added may be three points, two points, and one point in a case in which importance degrees of the organs in the current image are respectively high, medium, and low.

In addition, in Step S215, a score which differs in the importance degree of the organ of the current image is subtracted from the matching degree score. The amount of the score decremented may be three points, two points, and one point in a case in which importance degrees of the organs in the current image are respectively high, medium, and low.

In addition, in Step S224, a score which differs in the importance degree of the organ of the candidate image is subtracted from the matching degree score. The amount of the score decremented may be three points, two points, and one point in a case in which importance degrees of the organs in the candidate image are respectively high, medium, and low.

In this manner, the weighted matching degree score which is weighted with the importance degree of the organ is calculated. The matching degree between the organ in the current image and the organ in the candidate image can be represented by a degree at which an importance degree is added thereto when browsing the organs using the weighted matching degree score.

When the weighted matching degree score is used, an appropriate candidate image due to an aim for browsing of the user can be displayed as a new current image according to the part moving instruction by a user.

(Another Modification Example)

Although the image display system according to the exemplary embodiments of the invention has been described, the invention is not limited to the exemplary embodiments. As long as not being departed from the gist of the invention, various modifications conceivable by the skilled in the art which are applied to these exemplary embodiments, or aspects formed by combining the configuration components in other exemplary embodiments may be included in a range of one or a plurality of aspects of the invention.

For example, in the exemplary embodiments, an example is described, that, at the time of moving to the adjacent part, the current image is switched to an image, in which a matching degree of the organ with the current image among a plurality of images in the adjacent part is maximum. Such switching of the current image is not only performed at the time of moving to the adjacent part, but also performed at the time of moving to an arbitrary part.

In the exemplary embodiments, when image display device 200 starts to operate, first, the part list screen of FIG. 6 is displayed, and the current image displaying screen of FIG. 7 displays an image of an outermost layer of a part selected on the part list screen as a current image.

With respect to that, it is thought that a case of returning to the part list screen from the current image displaying screen by a certain operation which is not illustrated, and moving to the selected arbitrary part from the part list screen. In this case, since the exemplary embodiments intend to movement of the part from the current image displayed as described above, if the image of the outermost layer in the movement target part is displayed as a new current image following the process described above, there is a high possibility that a point of interest cannot be smoothly moved to the movement target part.

Here, at the time of moving to the arbitrary part through the part list screen from the current image displaying screen, an image, of which a matching degree of the organ with the recently displayed current image is maximum among the plurality of images of the movement target part, is displayed as a new current image. Accordingly, the user can smoothly move the point of interest to the movement target part at the time of moving from the current image displaying screen to the arbitrary part as well.

For example, the part arrangement information may indicate a position of each part of the entire diagram of a human body, instead of indicating an adjacency relationship of the parts.

FIG. 14 is a diagram illustrating an example of the part arrangement information according to a modification example.

In part arrangement information 130a illustrated in FIG. 14, a part position which is a position of a representative point of a part in the entire diagram of the human body is represented by correlating with a part name. The part position may indicate an approximate center of the image of the part. The part position is represented by a two-dimensional coordinate if the entire diagram of the human body is a general planar image, and is represented by a three-dimensional coordinate if the entire diagram of the human body is a parallax stereoscopic image.

In FIG. 14, as an example, the right chest part and the right upper limb respectively indicate positions Q1 and Q2 in the entire diagram of the human body.

Figure 15:
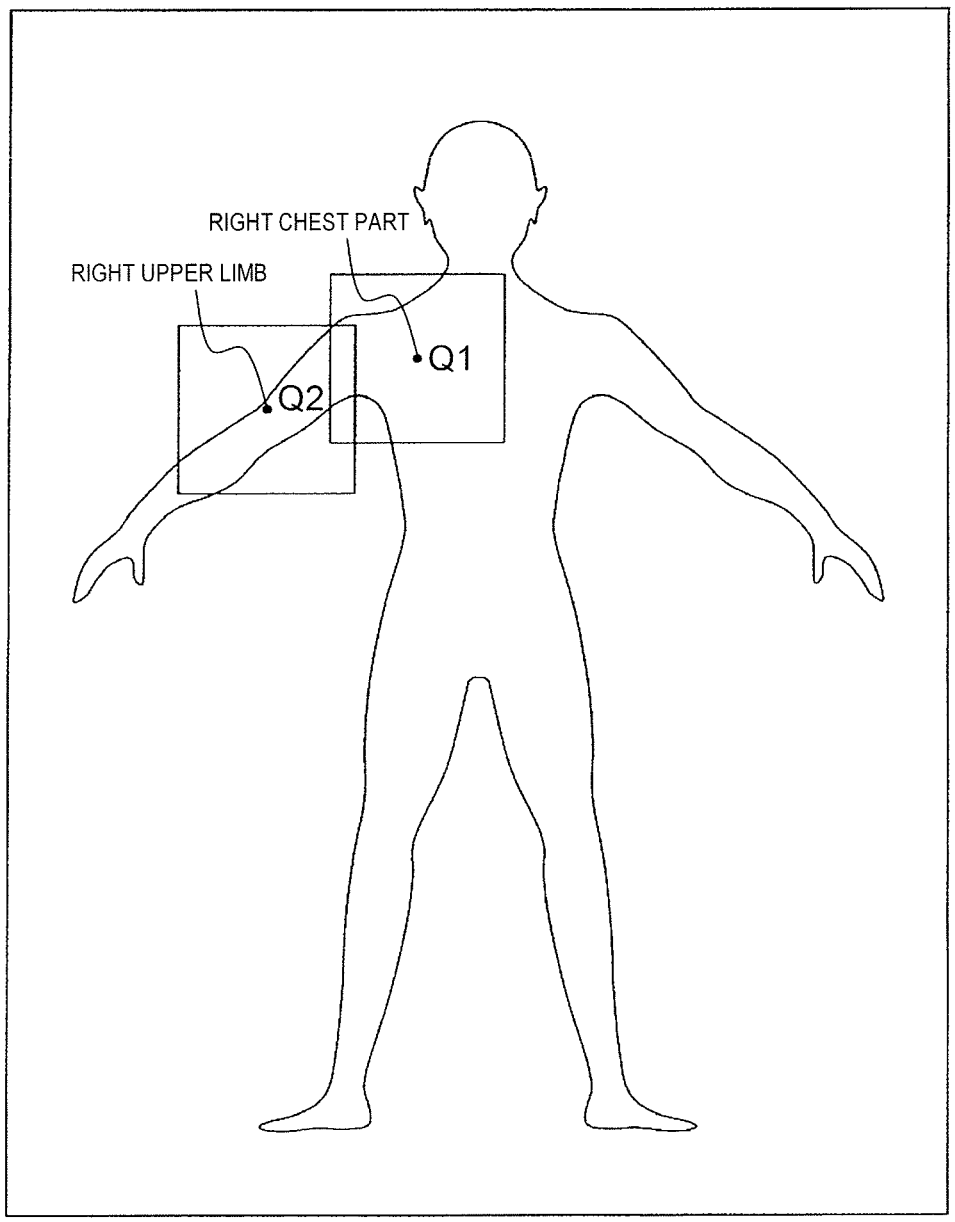
FIG. 15 is an explanatory diagram schematically illustrating a specific example of the part arrangement information according to the modification example.

FIG. 15 is an explanatory diagram schematically illustrating a specific example of part arrangement information 130a.

FIG. 15 illustrates each of positions Q1 and Q2 of the right chest part and the right upper limb in the entire diagram of the human body according to part arrangement information 130a of FIG. 14. An approximate size of the image may be indicated by a rectangular frame surrounding positions Q1 and Q2.

According to such a part arrangement information 130a, a distance and a direction between the two parts are calculated by calculation of a coordinate from the part positions of two parts. The same process as the process described in the exemplary embodiments can be performed on two parts positioned at a distance of a predetermined threshold or less as the adjacent parts. A list of the part positions in the entire diagram of the human body can be displayed on the part list screen as an aspect as illustrated in FIG. 15.

In addition, when part movement is performed in a case in which a plurality of multilayered anatomical images are present on the same part, for example, in a case in which an image for brain surgery of a brain surgery and an otolaryngology images for otolaryngology are present on the same part, an image having a high matching degree as described above may be selected, or the image for brain surgery which is set for the brain surgery in advance may be preferentially displayed, that is, an image having a high matching degree among the images for the brain surgery may be displayed.

Finally, the entire hardware configuration of image display system 1 will be described.

Figure 16:
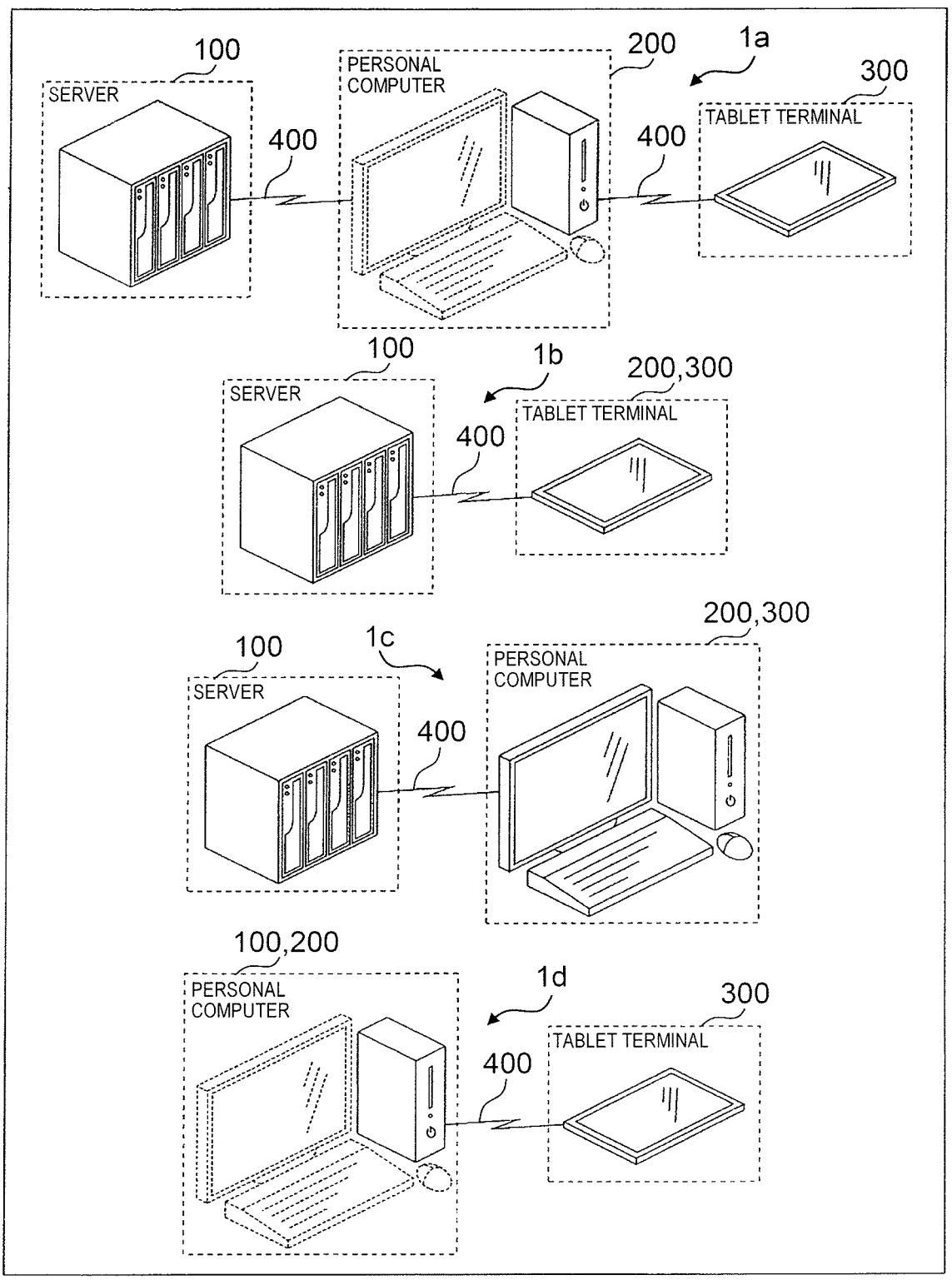
FIG. 16 is a diagram illustrating an example of the entirety of a hardware configuration of the image display system.

FIG. 16 is a diagram illustrating an example of the entire hardware configuration of image display system 1.

Basically, as illustrated in image display system 1a, storage device 100 may be constituted by a server, image display device 200 may be constituted by a personal computer, and inputting and outputting device 300 may be constituted by a tablet terminal. In this configuration, a display, a keyboard, and a mouse of the personal computer are not used as inputting and outputting device 300.

Communication path 400 is connected in a wired or wireless manner between storage device 100 and image display device 200 and between image display device 200 and inputting and outputting device 300. In communication path 400, Internet or a local area network in a hospital or in a campus can be used.

In addition, in a case in which the tablet terminal has a sufficient calculating performance, as illustrated in image display system 1b, image display device 200 and inputting and outputting device 300 may be configured with the tablet terminal.

In addition, as a case in which a desk top is assumed to be used, as illustrated as image display system 1c, image display device 200 and inputting and outputting device 300 may be constituted by a personal computer. In this configuration, a display, a keyboard, and a mouse of the personal computer are used as inputting and outputting device 300.

In addition, in a case in which local operation is assumed to be used, as illustrated as image display system 1d, storage device 100 and image display device 200 may be constituted by a personal computer.

In a case in which a standalone is assumed to be used, it is not illustrated, but all of storage device 100, image display device 200, and inputting and outputting device 300 may be constituted by only a personal computer, or only a tablet terminal.

As seen from the above, image display system 1 can be realized by various hardware configurations which are not limited.

As described above, inventors of the invention found that following problems occur with respect to the image display disclosed in the background.

As described above, in the image display system that the inventors of the invention are studied, the plurality of images obtained by performing the multilayered anatomy on each of the plurality of parts of the human body are proposed to the user.

In the multilayered anatomy, anatomy is performed on one part of the human body in a local and multilayered manner, and an organ in accordance with a purpose (for example, intention of diagnosis and treatment department) of the multilayered anatomy in each layer is anatomized. Because of a difference between the parts on which the multilayered anatomy is performed or a difference of purposes thereof even in the multilayered anatomy performed on the same part, layers of different multilayered anatomies do not relate to one another. Therefore, problems as follows may occur.

For example, the user instructs movement to an adjacent part when browsing an image of one layer in one multilayered anatomy. At this time, the image display system switches the display to any one image among the plurality of images obtained by a separate multilayered anatomy performed on the adjacent part.

However, since the layers in the different multilayered anatomies are not related to each other, it is not clear that any image of which layer on the adjacent part is an appropriate image to switch the displaying. The image display system, for example, is capable of switching the display to an image (for example, body surface layer) of a prescribed layer or an image of an arbitrary layer, but even when such switching is performed, the user can not always smoothly move a point of interest.

Here, this disclosure is to provide the image display device which is capable of displaying an appropriate image according to the part moving instruction from the user.

The image display device according to one aspect of the disclosure is provided with the image outputting unit, the part moving unit, and the matching degree score calculating unit. The image outputting unit outputs, among a plurality of images obtained by performing a multilayered anatomy and photographing the organ in a plurality of parts of a human body, an image of one layer in the multilayered anatomy of one part as a current image. The part moving unit acquires a part moving instruction which instruct to display a different part from the part of the current image after the current image is output. The matching degree score calculating unit calculates the matching degree score indicating a matching degree between the at least one organ included in the candidate image and the at least one organ included in the current image by comparing the label information indicating the organ included in the current image with the label information indicating the organ included in the candidate image, with respect to each of the plurality of candidate images which are the images of individual layer corresponding to a part instructed to be displayed by the part moving instruction in the plurality of images. The image outputting unit outputs the candidate image in which a maximum matching degree score is calculated as a new current image.

According to such a configuration, in accordance with the part moving instruction by a user, the displaying can be switched from the current image to a candidate image with the maximum matching degree of the at least one organ with respect to the current image among the plurality of candidate images in the movement target part. As a result, the user can browse the candidate image in which the matching degree is maximum continuous to the current image, and thus a point of interest can be smoothly moved to the movement target part.

In addition, the matching degree score calculating unit may add the matching degree score when there is an organ which is included in not only the current image but also the candidate image.

According to such a configuration, the candidate image further including the current images and the common organs is displayed as a new current image. As a result, the user is less likely to lose the organ, for example, in a case of tracking and referring traveling of the blood vessel or the nerve on the image, and can smoothly move the point of interest to the movement target part.

In addition, the matching degree score calculating unit may decrement the matching degree score when there is an organ which is included in the current image but not included in the candidate image.

According to such a configuration, the candidate image in which the missing organs with respect to the current image are fewer is displayed as a new current image. As a result, losing of attentiveness of a user due to the missing organ in the image of the movement target part is reduced, and thereby making it possible to smoothly move the point of interest to the movement target part.

In addition, the matching degree score calculating unit may decrement the matching degree score when there is an organ which is included in the candidate image but not included in the current image.

According to such a configuration, the candidate image in which the extra organs with respect to the current image are fewer is displayed as a new current image. As a result, losing of attentiveness of the user due to the extra organ in the image of the movement target part is reduced, and thereby making it possible to smoothly move the point of interest to the movement target part.

In addition, the matching degree score calculating unit may determine at least one of the additional amount of the matching degree score and the decrement amount of the matching degree score, in accordance with importance degree information indicating an importance degree of the organ included in the current image and importance degree information indicating an importance degree of the organ included in the candidate image.

According to such a configuration, the weighted matching degree score which is weighted with the importance degree of the organ is calculated. The matching degree between the organ in the current image and the organ in the candidate image can be represented by a degree at which an importance degree is added thereto when browsing the organs using the weighted matching degree score. When the weighted matching degree score is used, an appropriate candidate image suitable for the user's objective of browsing can be displayed as a new current image according to the part moving instruction by a user.

In addition, the image display system according to one aspect of the disclosure is provided with the image display device, the storage device, and the inputting and outputting device. The storage device includes at least one of the plurality of images, the label information, and the importance degree information. The inputting and outputting device includes a display unit which proposes the current image and the new current image output from the image outputting unit to a user, and an operating unit which receives the part moving instruction from the user.

According to such a configuration, an image processing system which exerts an effect described above is obtained.

In addition, the image display method according to one aspect of the disclosure outputs, among the plurality of images obtained by performing the multilayered anatomy and photographing the organ on the plurality of parts of the human body, an image of one layer in the multilayered anatomy on one part, as the current image. In addition, after the current image is output, the part moving instruction indicating a different part from the part of the current image is obtained. In addition, with respect to each of the plurality of candidate images which are images of individual layers corresponding to a part displayed by the part moving instruction in the plurality of images, the matching degree score indicating a matching degree between the at least one organ included in the candidate image and the at least one organ included in the current image is calculated by comparing the label information indicating the organ included in the current image and the label information indicating the organ included in the candidate image. The candidate image in which a maximum matching degree score is calculated is output as a new current image.

According to such a procedure, an image processing method exerting an effect described above is obtained.

In addition, a program according to one aspect of the disclosure may be a program for causing a computer to execute the image display method.

According to such a configuration, the effect described above can be exerted by a computer.

Moreover, these general or specific aspects may be realized by systems, methods, integrated circuits, computer programs, or recording mediums such as computer readable CD-ROMs, or may be realized by an arbitrary combination of the systems, methods, integrated circuits, computer programs, or recording mediums.

INDUSTRIAL APPLICABILITY

The invention is useful as a medical image display device.

REFERENCE MARKS IN THE DRAWINGS 1, 1a, 1b, 1c, 1d image display system
100 storage device
110 image information
120, 120a label information
130, 130a part arrangement information
200 image display device
210 image outputting unit
220 part selecting unit
230 layer moving unit
240 matching degree score calculating unit
250 part moving unit
300 inputting and outputting device
310 display unit
320 operating unit
331 thumbnail image
332 part name
340 current image
341 layer moving bar
342 part moving button
400 communication path

The invention claimed is:

1. An image display device comprising:
a memory storing instructions; and
a processor that, when executing the instructions stored in the memory, perform operations including:
outputting, among a plurality of images obtained by performing a multilayered anatomy and photographing organs in a plurality of parts of a human body, an image of one layer in the multilayered anatomy of one part as a current image;
acquiring a part moving instruction which instructs to display a different part from the part of the current image after the current image is output; and
calculating a matching degree score indicating a matching degree between at least one organ included in a candidate image and at least one organ included in the current image, with respect to each of a plurality of candidate images which are the plurality of images of individual layers corresponding to a part instructed to be displayed by the part moving instruction in the plurality of images, wherein the matching degree score is based on an existence of an organ commonly included in the current image and in the candidate image,
wherein the outputting outputs the candidate image in which a maximum matching degree score is calculated as a new current image.

2. The image display device of claim 1,
wherein, in the calculating, the processor adds the matching degree score for each organ which is commonly included in the current image and in the candidate image.

3. The image display device of claim 1,
wherein, in the calculating, the processor decrements the matching degree score for each organ which is included in the current image but is not included in the candidate image.

4. The image display device of claim 1,
wherein, in the calculating, the processor decrements the matching degree score for each organ which is included in the candidate image but is not included in the current image.

5. An image display system comprising:
the image display device of claim 1;
a storage device that stores at least one of the plurality of images and label information indicating the organ included in the current image and the organ included in the candidate image; and
an inputting and outputting device that includes a display which presents the current image and the new current image which are output from the image display device to a user, and an operator which receives the part moving instruction from the user.

6. The image display device of claim 1, wherein in the calculating, the processor calculates the matching degree score by comparing label information indicating the organ included in the current image with label information indicating the organ included in the candidate image.

7. An image display device comprising:
a memory storing instructions; and
a processor that, when executing the instructions stored in the memory, perform operations including:
outputting, among a plurality of images obtained by performing a multilayered anatomy and photographing organs in a plurality of parts of a human body, an image of one layer in the multilayered anatomy of one part as a current image;
acquiring a part moving instruction which instructs to display a different part from the part of the current image after the current image is output; and
calculating a matching degree score indicating a matching degree between at least one organ included in a candidate image and at least one organ included in the current image, with respect to each of a plurality of candidate images which are the plurality of images of individual layers corresponding to a part instructed to be displayed by the part moving instruction in the plurality of images,
wherein, in the outputting, the processor outputs the candidate image in which a maximum matching degree score is calculated as a new current image, and
in the calculating, the processor determines at least one of an additional amount and a decrement amount of the matching degree score, in accordance with importance degree information indicating an importance degree of the organ included in the current image and importance degree information indicating an importance degree of the organ included in the candidate image.

8. The image display device of claim 7, wherein in the calculating, the processor calculates the matching degree score by comparing label information indicating the organ included in the current image with label information indicating the organ included in the candidate image.

9. An image display system comprising:
the image display device of claim 7;
a storage device that stores at least one of the plurality of images and label information indicating the organ included in the current image and the organ included in the candidate image; and an inputting and outputting device that includes a display which presents the current image and the new current image which are output from the image display device to a user, and an operator which receives the part moving instruction from the user.

10. An image display method comprising:

outputting, among a plurality of images obtained by performing a multilayered anatomy and photographing organs in a plurality of parts of a human body, an image of one layer in the multilayered anatomy of one part as a current image;

acquiring a part moving instruction which displays a different part from the part of the current image after the current image is output;

calculating a matching degree score indicating a matching degree between at least one organ included in a candidate image and at least one organ included in the current image, with respect to each of a plurality of the candidate images which are images of individual layers corresponding to a part displayed by the part moving instruction in the plurality of images, wherein the matching degree score is based on an existence of an organ commonly included in the current image and in the candidate image; and outputting the candidate image in which a maximum matching degree score is calculated as a new current image.

11. A non-transitory computer-readable recording medium that stores a program causing a computer to execute the image display method of claim 10.

12. The image display method according to claim 10, wherein the calculating calculates the matching degree score by comparing label information indicating the organ included in the current image with label information indicating the organ included in the candidate image.

13. An image display method comprising:

outputting, among a plurality of images obtained by performing a multilayered anatomy and photographing organs in a plurality of parts of a human body, an image of one layer in the multilayered anatomy of one part as a current image;

acquiring a part moving instruction which displays a different part from the part of the current image after the current image is output;

calculating a matching degree score indicating a matching degree between at least one organ included in a candidate image and at least one organ included in the current image, with respect to each of a plurality of the candidate images which are images of individual layers corresponding to a part displayed by the part moving instruction in the plurality of images; and outputting the candidate image in which a maximum matching degree score is calculated as a new current image, wherein the calculating determines at least one of an additional amount and a decrement amount of the matching degree score, in accordance with importance degree information indicating an importance degree of the organ included in the current image and importance degree information indicating an importance degree of the organ included in the candidate image.

14. The image display method according to claim 13, wherein the calculating calculates the matching degree score by comparing label information indicating the organ included in the current image with label information indicating the organ included in the candidate image.

* * * * *